United States Patent
Grabenkort et al.

[11] Patent Number: 5,263,497
[45] Date of Patent: Nov. 23, 1993

[54] ARMBOARD USEABLE WITH A MEDICAL DEVICE

[75] Inventors: Richard W. Grabenkort, Barrington, Ill.; Mary M. Carey, Kirkland, Wash.; Gerald G. Vurek, Mountain View, Calif.

[73] Assignee: Abbott Laboratories, Abbott Park, Ill.

[21] Appl. No.: 775,168

[22] Filed: Oct. 11, 1991

[51] Int. Cl.$^5$ ................................................. A61B 5/02
[52] U.S. Cl. .................................... 128/877; 128/878; 128/869
[58] Field of Search .................. 128/877, 77, DIG. 26, 128/DIG. 6, 896, 869, 878, 879; 602/1, 5, 9, 22, 23

[56] References Cited

U.S. PATENT DOCUMENTS

| | | | |
|---|---|---|---|
| 2,763,264 | 9/1956 | McInnerny | 128/214 |
| 2,858,540 | 11/1958 | Morrison | 2/34 |
| 3,059,645 | 10/1962 | Hasbrouck et al. | 128/346 |
| 3,256,880 | 6/1966 | Caypinar | 128/133 |
| 3,521,625 | 7/1970 | Mackey | 128/133 |
| 3,625,210 | 12/1971 | Mikkelson | 128/DIG. 6 X |
| 3,640,273 | 2/1972 | Ray | 128/87 |
| 3,722,508 | 3/1973 | Roberts | 128/DIG. 6 X |
| 3,788,307 | 1/1974 | Kistner | 128/77 |
| 3,812,851 | 5/1974 | Rodriguez | 128/DIG. 6 X |
| 3,831,467 | 8/1974 | Moore | 128/80 |
| 4,198,989 | 4/1980 | Hawke et al. | 128/DIG. 6 X |
| 4,254,766 | 3/1981 | Kordis | 128/87 |
| 4,265,232 | 5/1981 | Stonich | 128/133 |
| 4,286,588 | 9/1981 | Lovegrove | 128/133 |
| 4,290,425 | 9/1981 | Helfer et al. | 128/133 |
| 4,449,975 | 5/1984 | Perry | 604/179 |
| 4,470,410 | 9/1984 | Elliott | 128/133 |
| 4,561,857 | 12/1985 | Sacks | 128/DIG. 6 X |
| 4,846,807 | 7/1989 | Safadago | 128/DIG. 26 X |
| 4,870,976 | 10/1989 | Denny | 128/877 |

Primary Examiner—Robert A. Hafer
Assistant Examiner—Sam Rimell
Attorney, Agent, or Firm—Harry G. Thibault; Robert E. Wexler

[57] ABSTRACT

An improved armboard includes receptacles for receiving and holding a medical device to be used in conjunction with the treatment of a patient. The patient's forearm is immobilized on the armboard, a sensor associated with the medical device is inserted into the patient, with a side channel of the armboard holding the medical device and a cable extending from the sensor to a fiber optic connector received in a modular unit stored in a suitable cavity and optical cable channels extending from opposite ends thereof are appropriately sized to prevent misinsertion of the modular unit into the armboard. The armboard is formed from polystyrene foam, and thus is lightweight, disposable after a single use, and the cavities provided therein are appropriately sized to receive and retain the components of the medical device associated therewith.

8 Claims, 5 Drawing Sheets

ARMBOARD USEABLE WITH A MEDICAL DEVICE

BACKGROUND OF THE INVENTION

1. Field of the Invention

The present invention relates generally to devices for restraining the arm of a patient during a medical procedure and in particular to an armboard which restrains the arm of the patient during a medical procedure and also retains therein a medical device associated with such procedure.

2. Description of the Prior Art

It is known to restrain a patient's arm during a medical procedure such as intravenous injections in which an armboard will both support and restrain the patient's arm during blood transfusions, intravenous feedings and the like. Because patients who are being given blood transfusions or intravenous feedings are often restless and unable to control their extremities, the needles placed in the veins of the arms will tend to slip out before the injection is complete.

Accordingly, devices such as described in U.S. Pat. No. 2,763,264, entitled "Device Useful in Giving Intravenous Injections"—McInnerny were introduced. Such a device immobilizes the arm, using straps to hold the arm in place, and is cushioned to provide some comfort to the patient while the medical procedure associated with immobilizing the arm is performed. Typically, such devices are relatively rigid, designed to be reusable and are simply structured to immobilize the arm.

Variations on such a theme can be found in the armboards described in the U.S. Pat. Nos. 3,521,625; 4,265,232; 4,254,766; 3,788,307; 4,286,588; 3,256,880; and 3,640,273. Other devices primarily for restraint but allowing some movement are also known, such as the device described in U.S. Pat. No. 3,831,467 entitled "Knee Brace"—Moore and the device described in U.S. Pat. No. 2,858,540 entitled "Limb and Knee Protector"—Morrison.

However, a common problem associated with many of these devices is that there is a medical procedure conducted in association with the restraint of the arm, such as an intravenous feeding or a blood transfusion. Attempts to maintain the medical device in the arm during the course of such procedure can be seen in U.S. Pat. No. 3,059,645 entitled "Adjustable Clamp"—Hasbrook et al, and U.S. Pat. No. 4,449,975 entitled "Intravenous Anchor and Wound Shield"—Perry. Early attempts to combine these functions can be seen in U.S. Pat. No. 3,722,508 entitled "Infusion Guard and Mobilizer"—Roberts and U.S. Pat. No. 4,470,410 entitled "Protective Restraining Device and Method"—Elliott.

But as medical procedures become more sophisticated, it becomes apparent that the present devices cannot address all the needs of the patient undergoing the medical procedure or of the medical professionals administering such procedure. For example, an intravenous feeding or blood transfusion is a relatively short medical procedure requiring minutes to perform and thus the patient3 s arm can be left in a relatively immobile position during the term of such procedure and it is not necessary for the device associated therewith to have a great degree of mobility.

Moreover, the needles and tubing associated with such medical procedures are relatively sturdy and even though they may tend to be dislodged from the patient, they're not easily subject to breakage and therefore, such breakage is not a consideration in these devices.

SUMMARY OF THE INVENTION

However, there are a new generation of medical procedures which require sensors inserted into the bloodstream of a patient to remain there for hours and even days, and require a much more sophisticated device to restrain the patient. For example, in one instance fiber optic elements supporting a sensor are inserted into the patient's arm, a fiber optic cable includes an optical connector provided between the sensor and a processor associated with the medical procedure to accommodate a sensor/processor interface and the restrained arm is maintained in an optimum holding position for retention of the sensor in the bloodstream of the patient for the duration of the testing period. The fiber optic elements carried by the fiber optic cable and associated with the sensor inserted into the arm would be easily damaged if the armboard did not substantially restrict the patient's movement of his arm as well as maintain the arm in an optimum position for placement and retention of the medical device.

An armboard constructed in accordance with the present invention must not only maintain the patient's arm in a fixed position for an extended period of time, it must be relatively light to easily enable limited movement of the patient's arm while it is being retained in such optimum position for retention of the medical device in the arm.

Also, to be effective, the armboard must provide suitable receptacles for holding not only the medical device associated with the procedure, but also a modular unit holding the fiber optic connector disposed between the medical device and the processor unit. Moreover, the armboard must be so constructed as to maintain the associated fiber optic cable in a relatively stable position to minimize damage thereto. Accordingly, the present invention provides an improved armboard for immobilizing the forearm and wrist of the patient to enable insertion of a medical device into the arm. The improved armboard comprises a main body portion having a contoured upper face which supports the forearm and wrist of the patient in an optimum position for insertion and retention of the medical device in the arm of the patient. Straps affixed to the armboard secure the arm and wrist of the patient in an optimum position on an upper surface of the armboard and suitable receptacles provided in the armboard receive and hold components of the medical device.

Such receptacles include channels provided on opposite sides of the armboard so that the armboard may be used for right or left hand patients, such channel to receive the medical device.

A suitable cavity is provided in the main body portion of the armboard below the upper face to retain the modular unit associated with the medical device. Elongated channels extend fore and aft from the cavity which retains the modular unit, a first channel to receive a fiber optic cable associated with the medical device, a second channel to receive the fiber optic cable associated with the processor.

Such an improved armboard is extremely lightweight and despite being molded from a lightweight material, is relatively strong and relatively stable so as to immobilize the patient during an extended period of time, to secure and maintain the medical device and its associated modular unit in an optimum position which not only maintains the medical device in the patient but also protects the sensitive fiber optic elements associated with that medical device by directing them along a preferred and protected path during use.

Moreover, the improved armboard of the present invention is light enough to permit the patient mobility during medical processes which may require readings over a period of hours or even days. Thus the patient can easily move his arm in a limited fashion even though the armboard will restrain the patient's forearm and wrist in a preferred optimum position for retaining the medical device in a position for obtaining readings from the device inserted into the patient.

A better understanding of the improved armboard of the present invention and the advantages which it provides can be obtained from a careful reading of the detailed description set forth below, particularly when such detailed description is considered in conjunction with the drawings provided.

DETAILED DESCRIPTION OF THE PREFERRED EMBODIMENT

Figure 1:
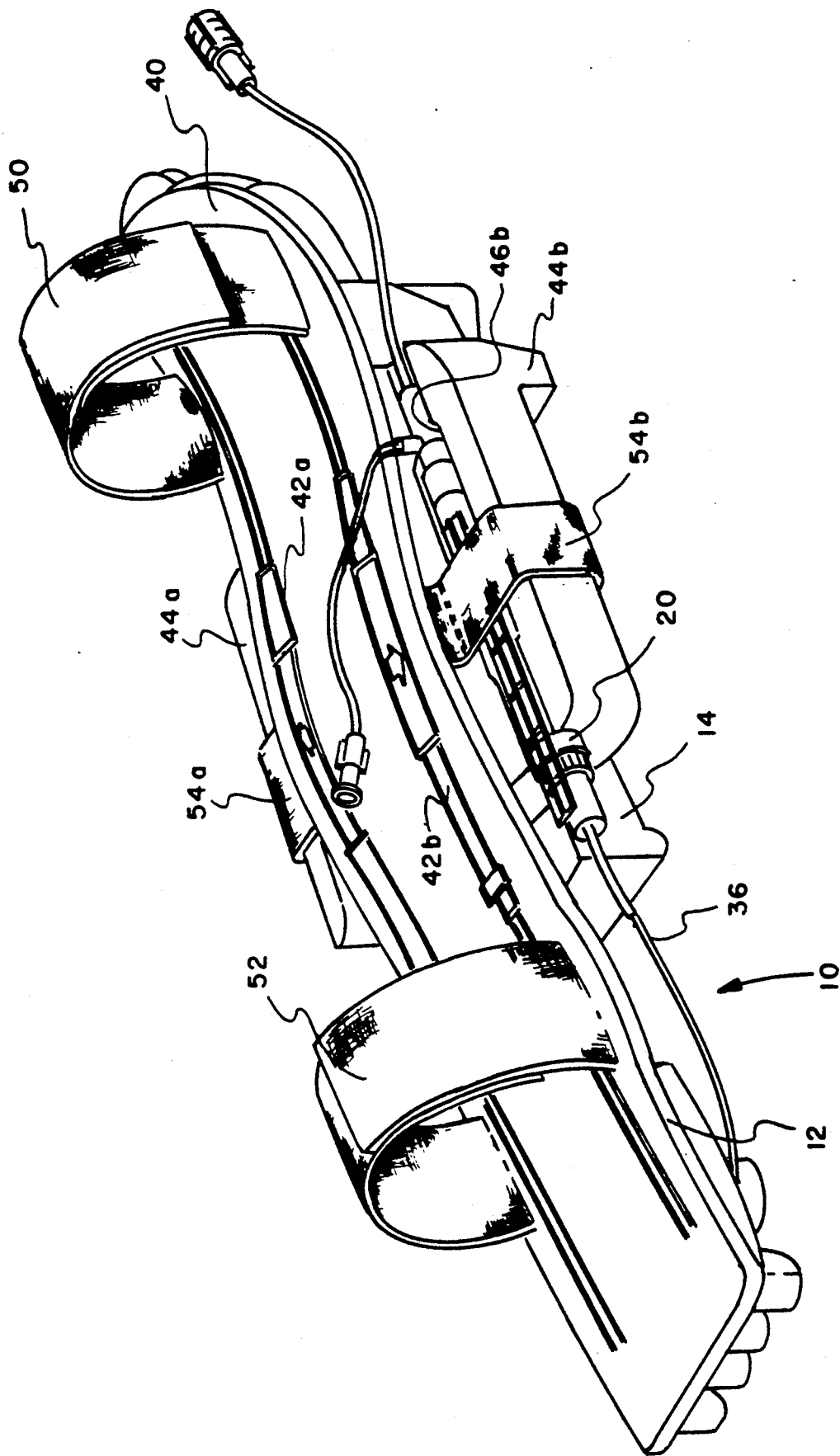
FIG. 1 is a top perspective view of the improved armboard of the present invention, with a medical device mounted on the armboard.
Figure 2:
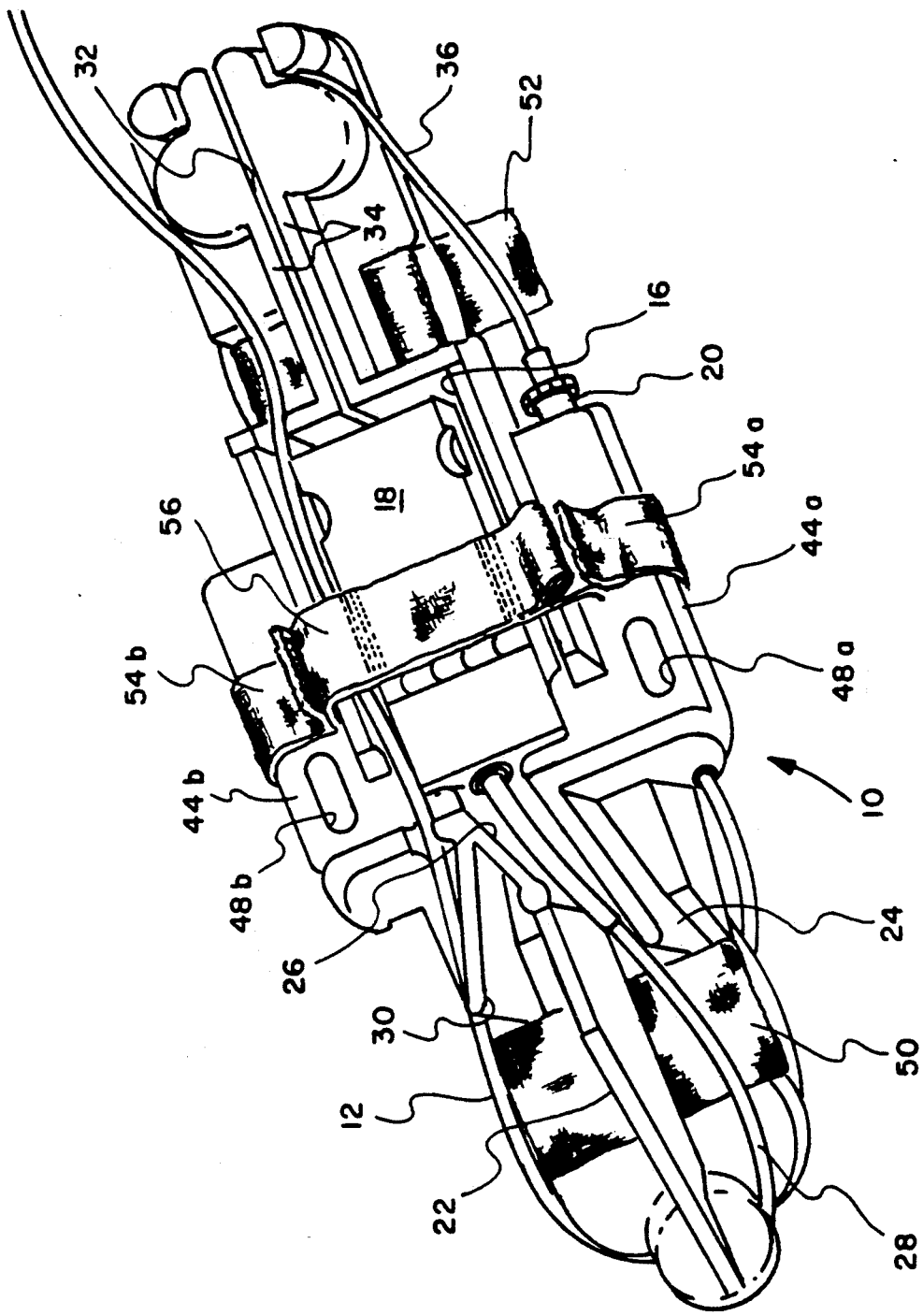
FIG. 2 is a bottom perspective view of the armboard of the present invention, with a modular unit and medical device mounted on the armboard.
Figure 3:
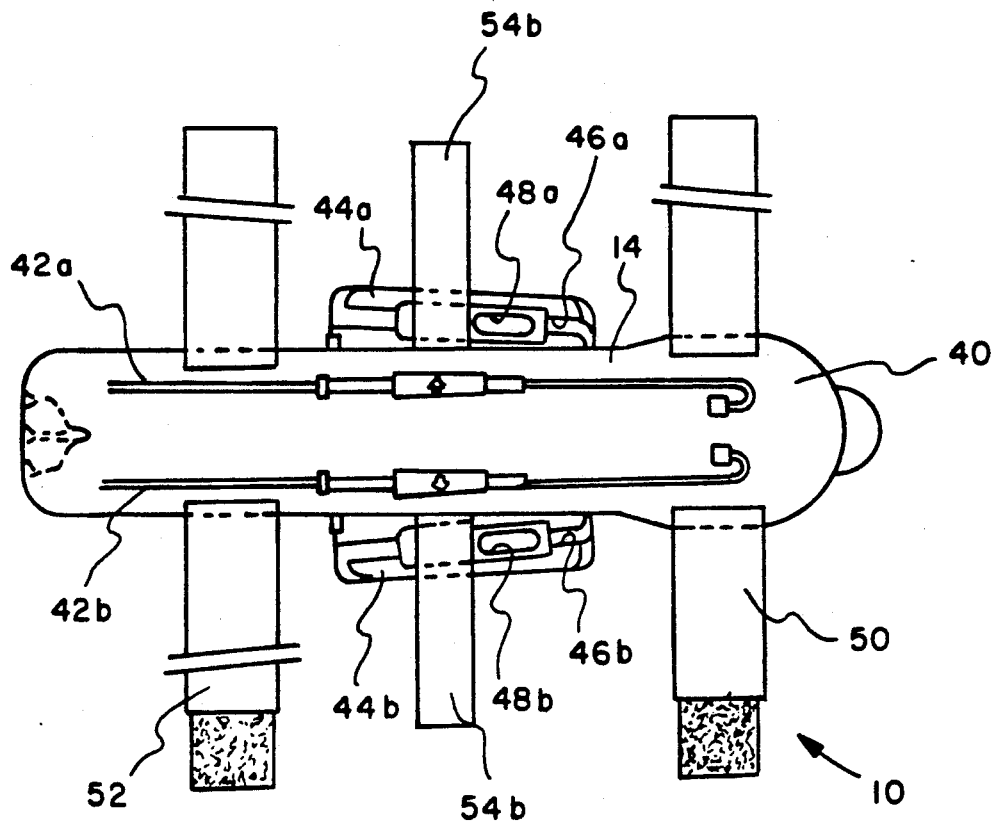
FIG. 3 is a top plan view of the armboard of the present invention.
Figure 4:
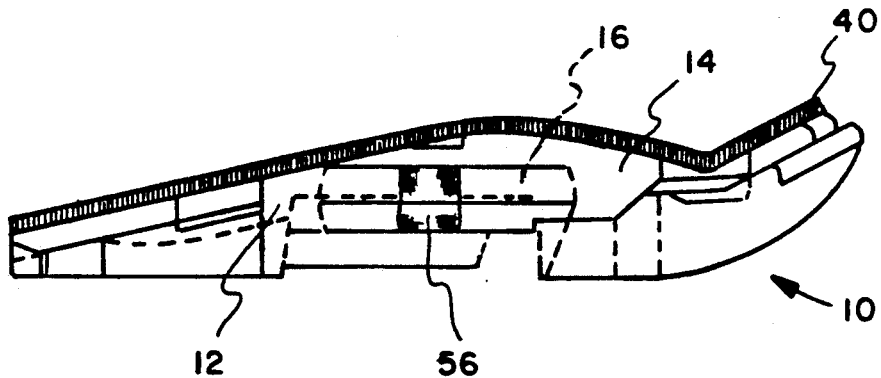
FIG. 4 is a side elevation of the improved armboard of the present invention, with the straps removed for clarity.

As shown in FIGS. 1-4, the improved armboard 10 of the present invention comprises an elongated main body portion 12. The main body portion 12 is preferably molded from a lightweight pliable material such as polystyrene foam. As can be seen from a careful examination of FIGS. 1-4, the polystyrene foam molded main body portion 12 stresses economy of design in which a central portion 14 of the main body portion includes a central cavity 16 for receiving a modular unit 18. The modular unit 18 is associated with a medical device 20, and both are described in greater detail below.

Extending forward of the central cavity 16 is a longitudinal rib 22 which terminates at the upper end of the main body portion 12 of the armboard 10. Disposed adjacent the longitudinal rib 22 is a second guide rib 24 which forms a channel 26 between the ribs 22 and 24 to provide egress for a processor cable 28 associated with a processor (not shown) connected to the modular unit 18 of the medical device 20. An additional support rib 30 is provided opposite the guide rib 24 to provide balance and support for the armboard 10 on the underside of the main body portion 14. Extending rearward of the central cavity 16 is a cable channel 32 defined by opposite channel members 34, the cable channel carrying therein a fiber optic cable 36 associated with the medical device 20 and connected between the medical device and the modular unit 18.

Glued to the upper face 38 of the main body portion 14 of the armboard 10 is a padding material 40 designed to cushion the forearm and wrist of the patient. Also provided on the padding 40 is a set of templates 42a, 42b directing the placement of the medical device 20 depending on whether the right forearm or left forearm of the patient is to be immobilized. In conjunction therewith are provided respective side members 44a and 44b, each having respective device receiving channels 46a and 46b and including respective openings 48a and 48b for the medical device 20. The member 44a is designated for immobilization of the left forearm and wrist of the patient whereas the member 44b is associated with the immobilization of the right forearm and wrist of the patient.

Also associated with the armboard 10 is an upper strap 50 which secures the wrist of the patient onto the armboard 10 and the lower strap 52 which secures the lower portion of the forearm of the patient to the armboard 10. In the preferred embodiment the straps 50 and 52 are simple VELCRO ® fasteners but of course any other form of strap which would suitably mobilize the patient's forearm and wrist are also usable in such application. In addition to the straps 50 and 52, there are also provided straps 54a and 54b associated with the respective left hand and right hand members 44a, 44b provided on the armboard. In the preferred embodiment of the present invention, the straps 54a and 54b are generally aligned with a strap 56 associated with the cavity 16 on the underside of the armboard 10 and used to retain the modular unit 18 within the cavity.

Used in conjunction with the armboard 10 is a site shield 58 (FIG. 5) described in greater detail in co-pending U.S. application Ser. No. 07/777,819, filed concurrently with the subject application and assigned to the assignee of the present invention. To the extent that such application will aid in the understanding of the present invention, the application is incorporated herein by reference.

Figure 5:
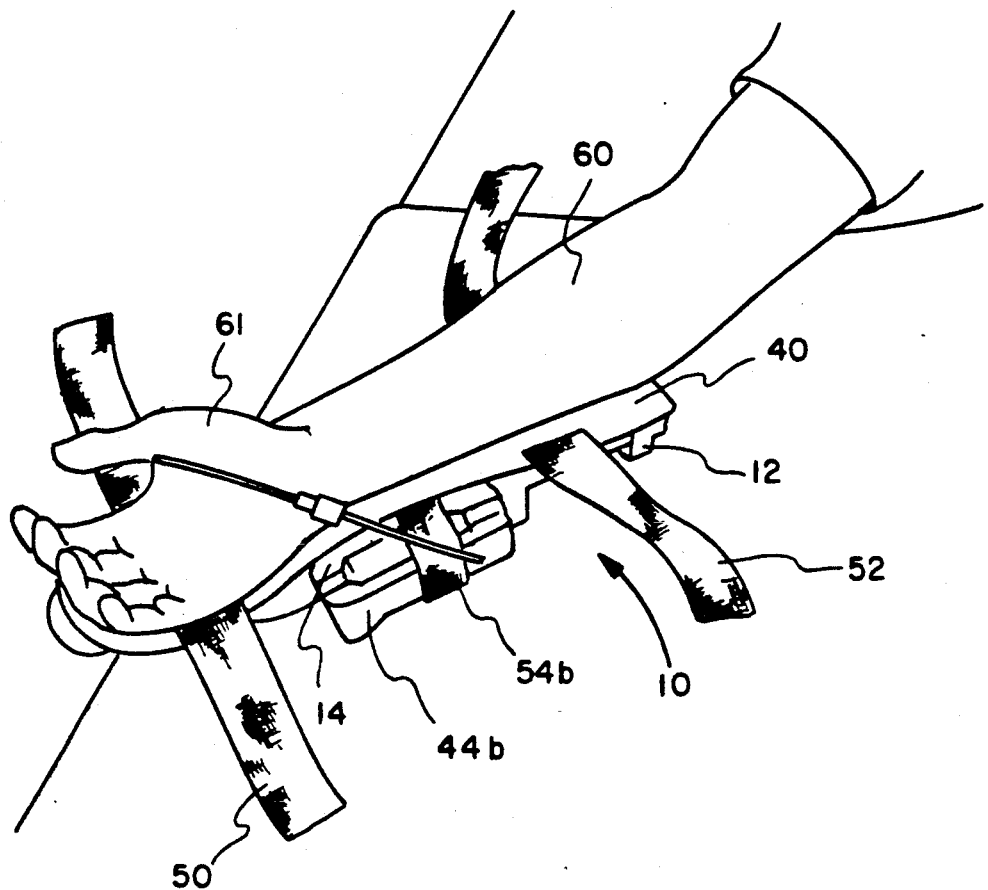
FIG. 5 is a top perspective view of the improved armboard showing a patient's right arm laid in place thereon.
Figure 6:
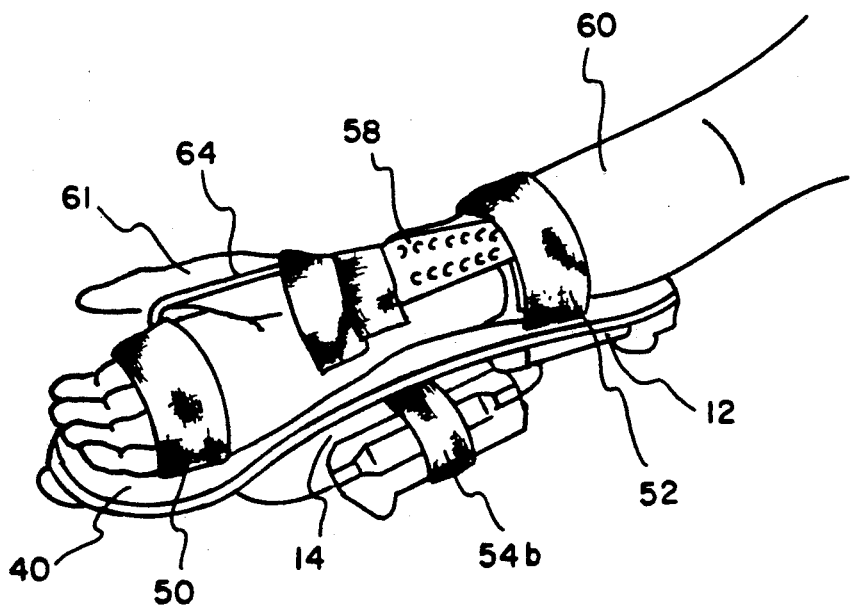
FIG. 6 is a top perspective view of the armboard of FIG. 4 showing the patient's right arm immobilized with a site shield in place.
Figure 7:
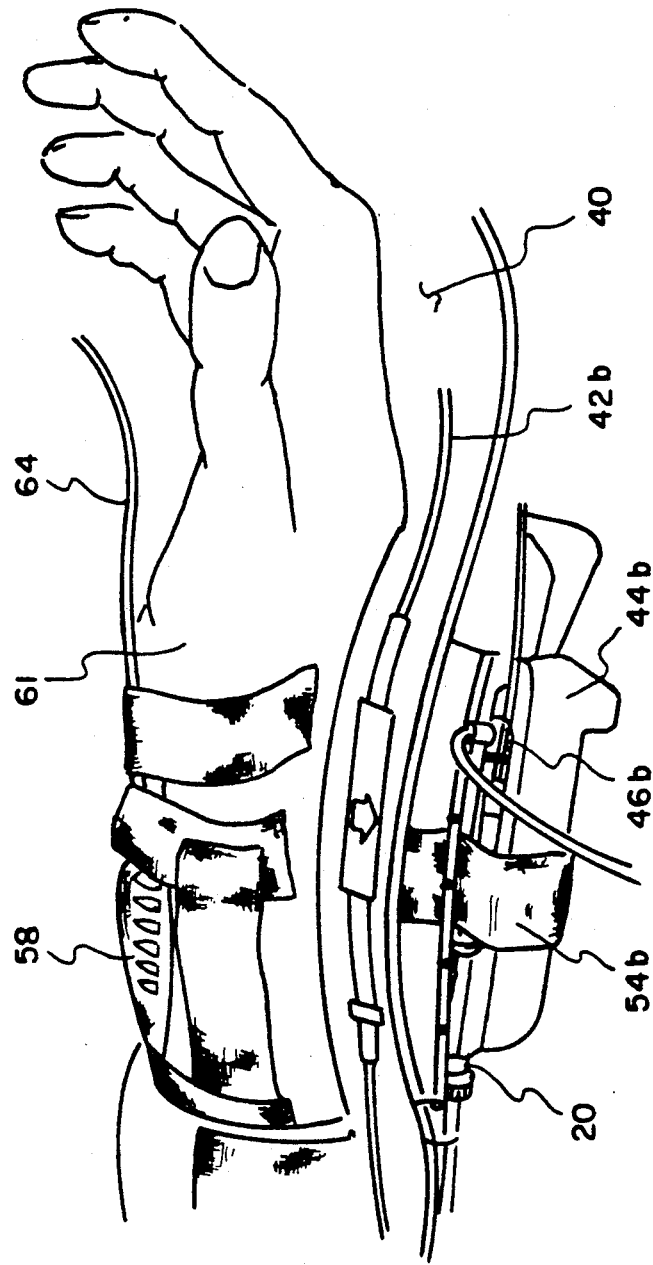
FIG. 7 is a detail view showing the medical device associated with the present invention in place.

FIGS. 5, 6 and 7 show how the armboard 10 is used in conjunction with the medical device 20. In FIG. 5, the right forearm 60 of the patient is laid palm up on the upper surface 14 of the armboard 10 with the straps 50 and 52 open. In FIG. 6 the straps 50 and 52 are closed over the right forearm 60 and hand 61 of the patient to immobilize the forearm and hand 60 of the patient on the armboard 10, the medical device 20 (FIG. 7) is placed in the channel 46b of the right hand member 46 with the catheter (not shown) inserted into the forearm 60 of the patient.

The medical device 20 comprises a fiber optic element which extends from the medical device, through catheter tubing 64 to a catheter (not shown) and there protected by the site shield 58. A sensor (not shown) is provided at the end of the fiber optic element and is delivered into the bloodstream of the patient A medical device or sensor delivery device 20 which could be used with the armboard 10 of the present invention is described in U.S. application Ser. No. 558,035, entitled Sensor Delivery Device and assigned to the assignee of the present invention.

The sensor delivery device 20 inserts the sensor into the bloodstream of the patient through the catheter tubing 64 and the catheter. The fiber optic elements supporting the sensor extend from the delivery device 20 through the fiber optic cable 36 to a disposable connector (not shown) at an opposite end of the cable 36, and which connects with a non-disposable fiber optic connector (not shown) mounted in the modular unit 18, at a non-disposable/disposable connector interface (not shown) thereof. The modular unit 18, the disposable and non-disposable fiber optic connectors and the connector interface are described in U.S. application Serial No. 629,321 entitled "Bevel Angle Fiber Optic Connector" and assigned to the assignee of the present invention, and the application is herein incorporated by reference to provide a better understanding of the fiber optical connector associated with the modular unit 18.

The central cavity 16 is conformed to receive the modular unit 18, which is necked down at the processor end, to prevent the modular unit from being incorrectly installed in the central cavity. Further safeguards against mis-installation are the wiring channels 36 and 32.

The channel 32 for the fiber optic cable 36 is substantially smaller than the processor cable 28. Thus the processor cable 28 will not fit in the channel 32 and the modular unit 18 must be correctly installed in the cavity 16 to correctly install the processor cable 28 in the channel 26 and the cable 36 in the channel 32. Note also that the cavity 16 is sized to receive and hold the modular unit 18 therein without the need for the strap 56. That is, the compliance of the polystyrene foam armboard 10 coupled with appropriate sizing of the cavity 16 and the modular unit 18 create a central cavity 16 which not only receives the modular unit, but also holds it in place without the aid of the strap 56. Similar construction of the channels 46a and 46b enables the user to mount the medical device 20 on the armboard 10 first, install the medical device in the patient and then immobilize the arm, a more convenient procedure for the health care worker.

Catheter tubing 64 is seen extending from the medical device 20 into the site shield 58 in FIG. 7. With the sensor delivery device 20 mounted in right hand channel 46b, with the catheter connected to the catheter tubing 64 appropriately inserted into the forearm 60 of the patient, the site shield 58 is suitably mounted in place to secure the catheter site. The sensor delivery device 20 is operated to insert a probe into the arm 60 through the catheter tubing 64 and the catheter to install a sensor associated with the sensor delivery device 20 into the bloodstream of the patient.

The fiber optic cable 36 associated with the medical device 20 extends from the lower end of the medical device through the channel 32 to connect to a non-disposable fiber optic connector (not shown) in the modular unit 18. The lower channel 32 defines a fixed, protected path for the fiber optic cable 36 associated with the medical device 20. The upper channel 26 provides a fixed and controlled path for the processor cable 28 associated with the modular unit 18.

By molding the armboard 10 from a relatively pliable material, such as polystyrene foam, the channels 46a, 46b which receive the tubular sensor delivery device 20, the channel 32 which receives the fiber optic cable 36 and the channel 26 which receives the processor cable 28 can be manufactured to relatively tight tolerances which enable them to retain and hold the respective cable or device securely therein, with the straps 54a, 54b associated with the device 20 merely providing an auxiliary holding function.

The polystyrene foam construction means that the armboard is inexpensively made, and disposable after a single usage. The present invention defines a relatively lightweight, inexpensive armboard which can immobilize a patient's forearm and wrist over an extended period of time, and yet permit limited movement of the patient's forearm while maintaining an optimum position for the patient's forearm in which the medical device can be held in place for monitoring the parameters of interest to be measured by the sensor associated with such medical device. Further the armboard includes compartments for holding and retaining the medical device 20 as well as the modular unit 18 associated therewith to permit the medical device and the modular unit to move in conjunction with movement of the armboard. Thus, such device provides freedom of movement, not only for the arm of the patient, but for the medical devices associated therewith while continuing to maintain such devices in an operative position in the arm of the patient.

We claim:

1. An improved armboard for immobilizing the forearm and wrist of a patient to enable insertion of a medical device into the arm, the improved armboard comprising an entirely rigid main body portion having a contoured upper face which supports the forearm and wrist of the patient in an optimum position for insertion and retention of the medical device in the arm of the patient;

straps for fixing and securing the forearm and wrist of the patient in said optimum position; and suitable receptacles provided int he armboard to receive and hold components of the medical device to be inserted into the arm of the patient; said receptacles including a central cavity disposed within the main body portion of the armboard and below the upper surface thereof to support and retain a modular unit associated with the medical device to be inserted into the patient, the central cavity so sized as to prevent mis-insertion of said modular unit.

2. An improved armboard as claimed in claim 1 wherein said receptacles include right and left side channels disposed adjacent the main body portion, with the selected side channel to support and retain a tubular component of the medical device to be inserted into an arm of the patient.

3. An improved armboard as claimed in claim 1 wherein a first wiring channel extends from a lower end of the central cavity to a lower end of the main body portion and a fiber optic cable extending from the tubular component of the medical device to the modular unit is supported and retained in said first wiring channel.

4. An improved armboard as claimed in claim 3 wherein a second wiring channel extends from an upper end of the central cavity toward an upper end of the main body portion to support and retain a processor cable associated with the modular unit.

5. An improved armboard as claimed in claim 4 which the fiber optic cable associated with the medical device and the processor cable are substantially different in size and the wiring channels provided in the armboard for the modular unit are respectively sized to selectively receive its corresponding cable, thus to prevent mis-insertion of the modular unit in the central cavity of the armboard.

6. An improved armboard as claimed in claim 1 wherein said armboard is a lightweight molded part, molded from a lightweight pliable polystyrene foam material to enable substantial movement of the arm by the patient even as the arm is retained in a fixed position by the armboard.

7. An improved armboard as claimed in claim 6 wherein said lightweight pliable polystyrene foam material enables very close tolerances between the components of the medical device and their respective receptacles to facilitate retention of said component within its respective receptacle.

8. An improved armboard as claimed in claim 1 wherein said receptacles include fasteners to secure each component of the medical device within its respective receptacle.

* * * * *